(12) United States Patent
Hsiung et al.

(10) Patent No.: US 7,638,157 B2
(45) Date of Patent: Dec. 29, 2009

(54) METHOD OF FABRICATING ELECTRODE ASSEMBLY OF SENSOR

(75) Inventors: Shen-Kan Hsiung, Taoyuan (TW); Jung-Chuan Chou, Yunlin (TW); Tai-Ping Sun, Taoyuan (TW); Wen-Yaw Chung, Taoyuan (TW); Li-Te Yin, Taipei (TW); Chung-We Pan, Pingtung (TW)

(73) Assignee: Chung Yuan Christian University, Taoyuan (TW)

( * ) Notice: Subject to any disclaimer, the term of this patent is extended or adjusted under 35 U.S.C. 154(b) by 501 days.

(21) Appl. No.: 11/533,358

(22) Filed: Sep. 19, 2006

(65) Prior Publication Data

US 2007/0023286 A1    Feb. 1, 2007

Related U.S. Application Data

(63) Continuation-in-part of application No. 10/287,598, filed on Nov. 5, 2002, now abandoned.

(51) Int. Cl.
*G01N 1/28* (2006.01)

(52) U.S. Cl. ............ 427/2.11; 427/58; 427/255.32; 427/313; 427/558; 427/595

(58) Field of Classification Search ............ 427/2.11, 427/255.32, 313, 558, 595, 58
See application file for complete search history.

(56) References Cited

U.S. PATENT DOCUMENTS

2004/0249227 A1*  12/2004  Klapproth et al. ........... 585/250
2007/0001253 A1*  1/2007   Hsiung et al. ............... 257/434

\* cited by examiner

*Primary Examiner*—Binh X Tran
(74) *Attorney, Agent, or Firm*—WPAT, PC; Justin King

(57) ABSTRACT

A method of fabricating an electrode assembly of a sensor is described. The sensor has a field effect transistor. The electrode assembly is separated from the field effect transistor by only a conductive line. The sensor is functioned to detect different glucose concentrations. A solid layer of tin oxide is deposited on a substrate board. A β-D-glucose oxidase and polyvinyl alcohol bearing styrylpyridinium groups are placed in 100 μl of sulfuric acid, to form an enzyme mixture. The enzyme mixture is dropped on the solid layer of tin oxide. The enzyme mixture is dried. The enzyme mixture is exposed to a UV ray. The enzyme mixture is dried and stabilized. The enzyme mixture is immersed in a sulfuric buffer.

4 Claims, 8 Drawing Sheets

(b)

METHOD OF FABRICATING ELECTRODE ASSEMBLY OF SENSOR

CROSS REFERENCE TO RELATED APPLICATIONS

This application is a continuation in part of applicant's earlier application, Ser. No. 10/287,598, filed Nov. 5, 2002.

BACKGROUND OF THE INVENTION

1. Field of Invention

This invention relates generally to a sensor, and more particularly to a method of fabricating an electrode assembly of a sensor.

2. Description of Related Art

Glass electrodes have many merits such as high linearity, good ion distinction, and stability. However, problems like the large size, high cost and long response time a reaction time have decreased their performance. In 1989 on pages 59-63, issue 1, volume 67 of the Int. J., B. D. Liu et al. illustrated the new direction in utilizing the mature field effect ion sensor developed by the mature silicon semiconductor integrated circuit process. The attempt was to replace the traditional glass electrode.

In 1970 on pages 70-71, volume BME-17 of IEEE Transactions Biomedical Engineering, Piet Bergveld first removed the metallic part of the poles of the metal-oxide-semiconductor field effect transistor (MOSFET). He then immerses the element into an aqueous solution; use the oxidation layer as an insulated ion sensor. This sensor produces different electrical potential at the interface when contacting solutions of different acidity, changing the electric current of the circuit to measure the pH or other ion concentration of the solution. Thus, Piet Bergveld named this sensor the ion sensitive field effect transistor (ISFET).

In the 70's, the development and application of the ISFET were still in an explorative stage. When the 80's arrived, the research on this field has reached a new dimension, whether in the basic theoretic research, key technologies, or practical applications. For example, dozens of ion and chemical field effect transistor based on the ISFET had been created, excelled in the microlization, modularization, and multifunction. The global popularity of the ISFET in a mere decade owed the credit from its distinctive characteristics described by D. Yu et al. in 1990 on pages 57-62, volume 1 of the Chemical Sensors, J. Sensor & Transducer Tech:

1. Minute size allowing micro solution measurements.
2. High input resistance and low output resistance.
3. Fast effect.
4. Compatible production process with the MOSFET technology.

Merits described above have fired a research fever on the ISFET within many research institutes in the past 2 decades. A brief outline of the international development of this element is noted below:

W. M. Siu and R. S. C. Cobbold reported an ISFET with silicon dioxide, silicon nitride, oxide, and aluminum oxide as ion sensors in 1979 on pages 1805 to 1815, issue 11, volume ED-26.

ISFET based on different elemental structures: such as back contact field effect ion sensor reported by A. S. Wong in his Ph.D. Thesis in Case Western Reserve University, 1985. Or the expanding ISFET reported by J. Van Der Spiegel et al. on pages 291-298, volume 4 of Sensors and Actuators B, 1983.

Microlization of the reference electrode reported by D. Yu on pages 53 to 57, volume 3 of Chemical Sensors, J. Sensor & Transducer Tech., 1991. Differential ISFET on pages 221 to 237, volume 11 of Sensors and Actuators, 1987.

On pages 237 to 239, volume 5 of Sensors and Actuators B, 1991, Atushi Saito reported the use of enzymes on the ISFET to detect metabolic messages in biology (for example: detection of glucose or oxygen level in the blood.) Theoretical research attachment bond module on pages 315 to 318 reported by L. K. Meixner on pages 315 to 318 on volume 6 of Sensors and Actuators B, 1992.

R. E. G. van Hal reported a study on wrapping materials on pages 17 to 26, volume 23 of Sensors and Actuators B, 1995. B. H. Van Der Schoot et al. reported an integration of measuring system and sensors on pages 239 to 241, volume 4 of Sensors and Actuators B, 1991.

M. Grattarola reported yet another study on the field effect ion sensor simulation on pages 813 to 819, issue 4, volume 39 of IEEE Transactions on Electron Devices, 1992.

Listed below are patents granted so far: U.S. Pat. No. 5,309,085 (May 3, 1994)—readout circuit as a biological ISFET. This circuit has a simple structure and easy integration. The circuit is composed of input terminals from two ISFET, one as an enzyme field effect transistor, the other as a reference field effect transistor. Immobilizing an enzyme to the electrode of the ISFET does the enzyme field effect transistor. This circuit has different magnifying functions to magnify and output the ion detection. The voltage effect of the ISFET is due to the temperature effect of unstable reference electrodes. Thus the benefits of the circuit can be recognized and the sensor can be adjusted. This ion sensitive filed effect transistor-biosensor can be integrated on one single chip with the measuring circuit, to minimize the size of the sensor.

U.S. Pat. No. 5,296,122 (Mar. 22, 1994)—hydrophobic thin film used as the reference electrode of the ion sensitive field effect transistor. This hydrophobic thin film can grow on the substrate via neutral electrolyte or electroplating. The apparatus includes a vacuum, an atom ray generator, a base, a cover board to control growth elements. This thin film is applicable to ion sensors such as ion sensitive field effect transistors and enzyme sensors.

U.S. Pat. No. 5,061,976 (Oct. 29, 1991)—ion sensitive field effect transistor with carbon gate insulated electrode. Conducting material, 2,6 xylenol is then coated. The ion sensitive field effect transistor exhibits high sensitivity to hydrogen ions, low time drift, high stability, and low light effect. If other ion selective thin film or enzymes are further coated on the 2,6 xylenol, different ions and metabolites of different concentrations can be detected.

U.S. Pat. No. 6,218,208 (Apr. 17, 2001)—hot steam plating or ratio frequency sputtering is used to produce a field effect ion sensor with a metal light cover. The structure: tin oxide/metal/silicon oxide multi-structure sensor and tin oxide/metal/silicon nitride/silicon nitride multi-structure sensor. Many excellent characteristics are associated with this device, such as Nernst Effect between pH 2 to pH 10—high linearity in the 56≈58 mV/pH range. One unique point is that this sensor effectively decreased light interference. Moreover, this process requires simple apparatus, low cost, and easy mass production. Inexpensive, disposable sensors can also be produced. Therefore this invention possesses extremely high feasibility and applicability among the ISFET.

U.S. Pat. No. 5,925,318 (Jul. 20, 1999)—an iron-detecting sensor. Iron compounds such as lactoferrin are immobilized on the surface of the potentiometric or acidic sensor. Reactions changes the potential or the pH value of the iron-detecting sensor, therefore this sensor detects such changes. This patent includes iron molecule ion compound ion sensitive field effect transistor and acidity paper tester.

U.S. Pat. No. 5,918,110 (Jun. 29, 1999)—this patent is on an multi-sensor including pressure and electrochemical sensor, based on the ion sensitive field effect transistor on a silicon substrate. A protective layer follows deposition of a nitride layer as an acidity sensor. Then a multi-silicon thin film is positioned on the top of the vacuum space. This area is the pressure sensor, and the readout of the sensor can be through the CMOS standard. The oxidized middle layer of the gaseous sensor is made by the removal of oxidized layer with the wet chemistry method. The platinum contact point and the attached protective layer are deposited by PECVD. The pressure sensor is made after the completion of the gaseous sensor layers.

U.S. Pat. No. 5,516,697 (May 14, 1996)—a simple, low-cost biosensor for detecting ion concentrations. Lactoferrin is immobilized on the sensor surface. Lactoferrin reacts with iron and expresses electricity, changing the electropotential or the surface potential of the acidic sensor. This property enables the biosensor to detect ion concentrations. The biosensor includes the ion sensitive field effect transistor, and acidity paper tester.

According to the current literature, there are some materials most frequently used as the sensing membrane of the pH sensor such as silicon dioxide, silicon nitride, Ta2O5, and aluminum oxide. Hung-Kwei Liao et al. reported the first-time completion of the ISFET with tin oxide as the sensing membrane in this laboratory on pages 410 to 415 of Proceedings of the 3rd East Asian Conference on Chemical Sensors (Seoul, Korea), 1997. Properties of this sensor include Nernst Effect. Within the range of 56~58 mV/pH, a high linearity, time stability, low drift, and a reaction speed of lower than 0.1 second were all achieved. This laboratory also developed a multi-layered sensor, deterring light interference: sensor film/metal/silicon dioxide multi-layer sensor and film layer/metal/silicon nitride/silicon dioxide multi-structured sensor. This light deterring structure has inspired the structure of the EGFET. This apparatus views the metallic light deterring layer as a potential, and is pulled out of the field effect transistor with a conductor line, connecting to an ion sensitive film. The ion sensitive film is thus completely separate from the field effect transistor, only connected through a wire. Therefore, the ion sensitive film part can be seen as a low-cost, disposable ion sensitive electrode or bio-electrode. The field effect transistor part can then seen as a reusable front readout circuit. Our laboratory has discovered that the traditional highly insulative inorganic sensitive materials such as silicon nitride, aluminum oxide and tallium oxide cannot be used in this apparatus. The reason is that high insulation results in higher capacitance effect and an extremely unstable Transient response. However, this EGFET measuring apparatus performs rather well with the non-insulation sensitive materials below: tin oxide, ITO, titanium nitride. Therefore our laboratory has successfully completed this EGFET apparatus. To add to the strength of this new invention, it has very low light sensitivity and a linear, adjustable temperature coefficient.

SUMMARY OF THE INVENTION

This invention illustrates a method of fabricating an electrode assembly of a sensor. The sensor has a field effect transistor. The electrode assembly is separated from the field effect transistor by only a conductive line. The sensor is functioned to detect different glucose concentrations.

A solid layer of tin oxide is deposited on a substrate board. A β-D-glucose oxidase and polyvinyl alcohol bearing styrylpyridinium groups are placed in 100 μl of sulfuric acid, to form an enzyme mixture. The enzyme mixture is dropped on the solid layer of tin oxide. The enzyme mixture is dried. The enzyme mixture is exposed to a UV ray. The enzyme mixture is dried and stabilized. The enzyme mixture is immersed in a sulfuric buffer.

The method may alternatively comprise the following steps. A solid layer of tin oxide is deposited on a substrate board. Two μl of 3-glycidyloxypropyltri-methoxysilane are dropped on the solid layer of tin oxide. The solid layer of tin oxide, the two μl of 3-glycidyloxypropyltri-methoxysilane (GPTS) and the substrate board are cured.

DETAILED DESCRIPTION OF THE INVENTION

Figure 1A:
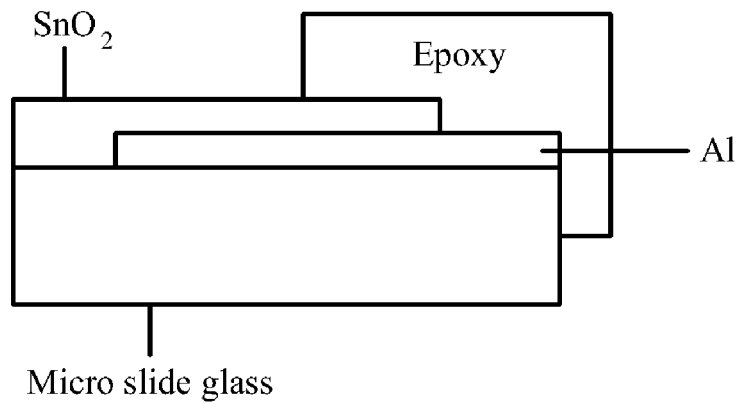
FIG. 1 schematically shows a sectional View of Types of Solid State Ion Sensitive Electrodes including:
(a) Micro Slide Glass as Sensor Substrate.
(b) Corning Glass as Sensor Substrate.
(c) ITO as Sensor Substrate.

In this invention, a potentiometric electrochemical sensor and biosensor based on an uninsulated solid-state material are presented.

This potentiometric electrochemical sensor and biosensor is different from the traditional ion sensitive field effect transistor (ISFET), wherein the sensing electrode is separated from the field effect transistor. Therefore the sensing electrode can be seen as a low cost disposable electrode. The sensing structure of this sensor is more rigid than the glass electrode, and the fabricative cost is lower than those of glass electrode and traditional ISFET electrode. In addition, this device shows a linear pH sensitivity of approximately 58~60 mV/pH with the high correlation coefficient up to 0.999 in a concentration range between pH2 and pH12. Therefore this device owns a good sensitivity and will not be affected by light interference.

INTRODUCTION

In this invention, an electrochemical potential sensor and a biosensor, based on an uninsulated solid-state material, are presented.

Electrochemical potential sensors and biosensors with this base are different from the traditional ion sensitive field effect transistor (ISFET), in that the sensing electrode of the new invention is separated from the field effect transistor, connecting to the field effect transistor by a mere metallic wire. Therefore the sensing electrode can be seen as a low cost, disposable electrode. Furthermore, the sensing structure of this sensor is more rigid than the commercial glass electrodes, and the cost is lower than those of the traditional ISFET and glass electrodes. In addition, this device shows a linear pH sensitivity of approximately 58~60 mV/pH with a high correlation coefficient over 0.999 in the pH range of 2 to 12. Therefore, this device possesses a high, linear sensitivity. To add to the strength of this invention, light interference of its performance is minimal.

Based on the above characteristics, a disposable sensor can be achieved. Thus, this invention has a high feasibility and applicability in electrochemical sensors and biosensors.

INDUSTRIAL APPLICABILITY

This invention illustrates the use of inorganic, non-insulated, solid state materials to create an electrochemical potential sensors and biosensors in a solid-state process.

FIGURE DESCRIPTION

1 ... $SnO_2$ (TiN, etc.)
2 ... Epoxy
3 ... Al
4 ... Micro slide glass
5 ... Corning 7059 glass
6 ... Conductive line
7 ... ITO
8 ... Glass substrate
21 ... Reference electrode, Ag/Ag Cl
22 ... Buffer solution
23 ... HP4145B
25 ... Reference electrode
26 ... Extended sensing gate ($SnO_2$/ITO glass or $SnO_2$/glass)
27 ... Bio-membrane/$SnO_2$/ITO/glass
31 ... Transconductance
32 ... pH=4
33 ... Drain current
34 ... pH=7
35 ... pH=10
36 ... pH=2
37 ... pH4→pH10
38 ... pH2→pH10
51 ... Linear line
52 ... Glucose solution
53 ... 12 minutes
54 ... Voltage Difference=19.5 mV
58 ... Glass
70 ... GOD+FcA
72 ... Epoxy
74 ... Conductive Line

DETAILED DESCRIPTION

In this invention, a sensor, such as an electrochemical potentiometric sensor or a biosensor based on a non-insulated solid-state material are presented. A sensor is different from a traditional sensor having an ion sensitive field effect transistor (ISFET). The difference includes a characteristic that the sensor has an electrode assembly separated from a field effect transistor by only a conductive line. With this characteristic, the electrode assembly is therefore a low cost and disposable electrode.

Electrochemical potentiometric sensors and biosensors with this characteristic are different from the traditional ion sensitive field effect transistor (ISFET), in that the sensing electrode of the invention is separated from the field effect transistor, connecting to the field effect transistor by a mere conductive line. Therefore the sensing electrode can be seen as a low cost, disposable electrode. Moreover, the structure of its sensitive electrode is stronger than the commercial glass electrode. Cost of the sensor is also lower than those of the traditional ion sensitive field effect transistor and glass electrode.

The abovementioned electrochemical potentiometric ion sensor made by uninsulated solid-state materials is unique in that an uninsulated solid-state ion sensor membrane (such as tin oxide) is deposited on the insulated or uninsulated substrate. A solid-state ion sensitive electrode is then formed to detect pH value of test solution. Conductive line is used as a message conductor, and wrapping materials such as epoxy is used to coat the non-sensitive areas. Sensitive area defined by the technology is about 3×3 mm2. The conductive line is connected to readout circuit of high input impedance, such as MOSFET and operation amplifier, to form the structure of the ion sensor. The advantage of this sensor over ordinary ISFET and glass electrodes are in that this new sensor is microlizable, easy to produce, low-cost, dry-storable, has low light interference, easy to pack, adjustable sensitive area, and convenient to deliver Moreover, this sensor has excellent characteristics; Nernst Effect is attained within pH2 to pH12. In the range of 58~60 mV/pH, the relative coefficient of linear regression is over 0.999. Thus the sensitive linearity is excellent. And the sensitivity to light is minimal. Therefore this invention is highly feasible in the application of electrochemical potentiometric sensors and biosensors.

This sensor is capable of transforming into an electrochemical potentiometric biosensor by immobilizing biochemical such as enzymes, immune substances, and nucleic acids. This effectively solves the problems of size and cost of the large photo-bio analyzers. The new sensor is suitable for portable, immediate detection and is disposable. The sensitive membrane of this ion sensor can be composed of tin oxide, titanium nitride, ITO, or $IrO_2$; it can also be used to detect hydrogen concentration. The solid sensitive membrane can be chosen based on the range and characteristics of the particular purpose. The insulation substrate of the structure and sensitive membrane may be comprised of silicon, glass, porcelain, or polymers. Therefore, this sensor has a better flexibility in the substrates and can be adjusted according to the practical needs and process conditions.

OPTIMUM EXAMPLE

Processing Conditions: this electrochemical ion sensitive electrode utilizes semiconductor membrane plating technology to deposit a solid sensitive membrane on the substrate. For bio-electrodes, a bio-enzyme is immobilized on the solid sensitive membrane.

A processing flow of fabricating an electrode assembly is illustrated as follows.

1. Prepare a variety of substrates (insulation material substrates, conductive substrates etc.). Then select one of the substrates to be a substrate board. The selection of substrate is based on the solid sensitive material and the environment of detection.
2. Clean the substrate board.
3. Deposit a solid layer of a solid-state sensitive material on the substrate board. The material is, for example, tin oxide or titanium nitride.
4. Wiring.
5. Seal with epoxy and secure an area of the sensitive window.
6. Form a membrane on the solid layer. The forming method includes, for example, immobilizing an enzyme membrane on the solid layer.

Steps 1 to 5 may be applied to potentiometric ion sensitive processing; steps 1 to 6 may be applied to biosensor processing.

β-D-glucose oxidase
β-D-glucose+O2→D-glucono-δ-lactone+H2O2

Glucose is broken down into D-glucono-δ-lactone and H2O2 with β-D-glucose oxidase catalysis.

D-glucono-δ-lactone→D-gluconate+H+

Through hydrolysis, H+ is produced. EGFET can detect changes in H+. Thus, concentrations of glucose or other substances can be detected by fastening the enzyme on the sensitive membrane of the extended ion sensitive field effect transistor.

Details on immobilizing the enzyme membrane, immune substances or nucleic acids:

Covalent coupling method, gel entrapment method, etc. can be used to immobilize enzyme membrane, immune substances or nucleic acids. As an example, the gel entrapment method and the enzyme membrane are described as follows.

Weigh out 5 mg of β-D-glucose oxidase and 50 mg of polyvinyl alcohol bearing styrylpyridinium groups (PVA-SbQ). Place the β-D-glucose oxidase and the polyvinyl alcohol bearing styrylpyridinium groups in 100 μl of sulfuric acid buffer, thereby forming an enzyme mixture.

Drop 1 μl of the enzyme mixture (β-D-glucose oxidase and PVA-SbQ) on a solid layer of tin oxide or ITO of a sensor. Dry the dropped enzyme mixture for 5 minutes to be a solid state.

Expose the dropped enzyme mixture on the solid layer, to a UV ray for about 20 minutes, for light polymerization.

Place the dropped enzyme mixture under 4° C., let the dropped enzyme mixture dry and stabilize for about 4 hours.

Immerse the dropped enzyme mixture in D.I. water for about 1 hour, to wash away unattached enzyme mixture from the solid layer.

Immerse the dropped enzyme mixture in sulfuric buffer for about 1 hour (5 mM, pH 8.08).

In the steps 2, 3 and 5≈6 of the entrapment method, the dropped enzyme mixture is not allowed to be exposed to a white light. This is to prevent light-induced polymerization of the dropped enzyme mixture.

Figure 1B:
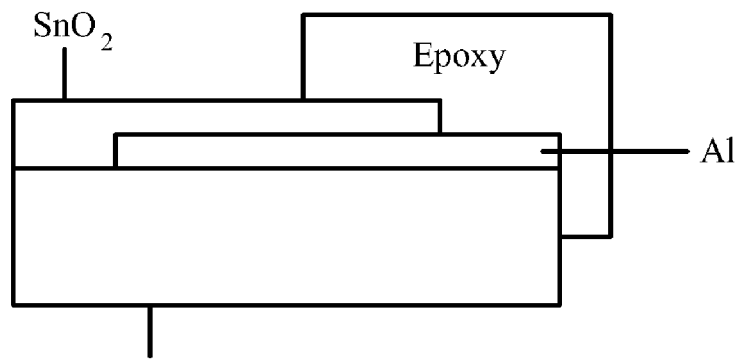
Figure 1C:
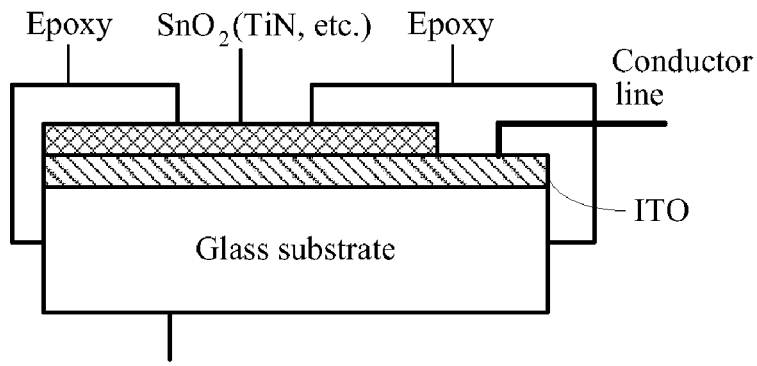
Figure 2:
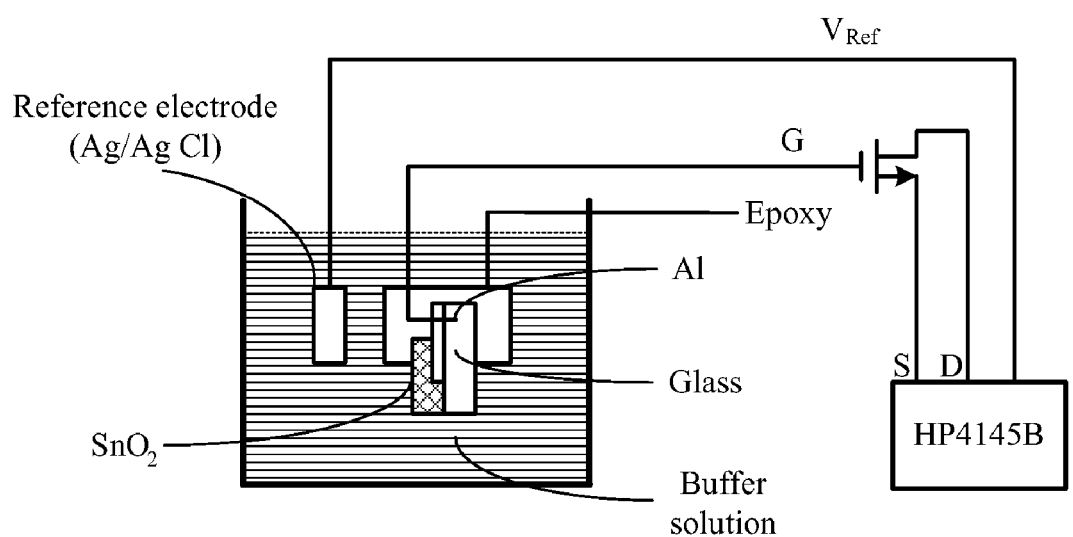
FIG. 2 schematically shows a measuring Apparatus of Sensor Electrode of I-V Properties.

Properties and Effects:

Shown in FIG. 1 is the Sectional Views of Solid State Ion Sensitive Electrodes. The pH value of a solution can be detected. The sensor substrate may be non-insulation glass, conductive glass, and other types of solid substrates. Shown in FIG. 2 is the Measuring figure of the I-V properties of this sensor. Using this measure, properties of the solid membrane can be analyzed and the pH sensitive property of the sensor can be confirmed.

Figure 3:
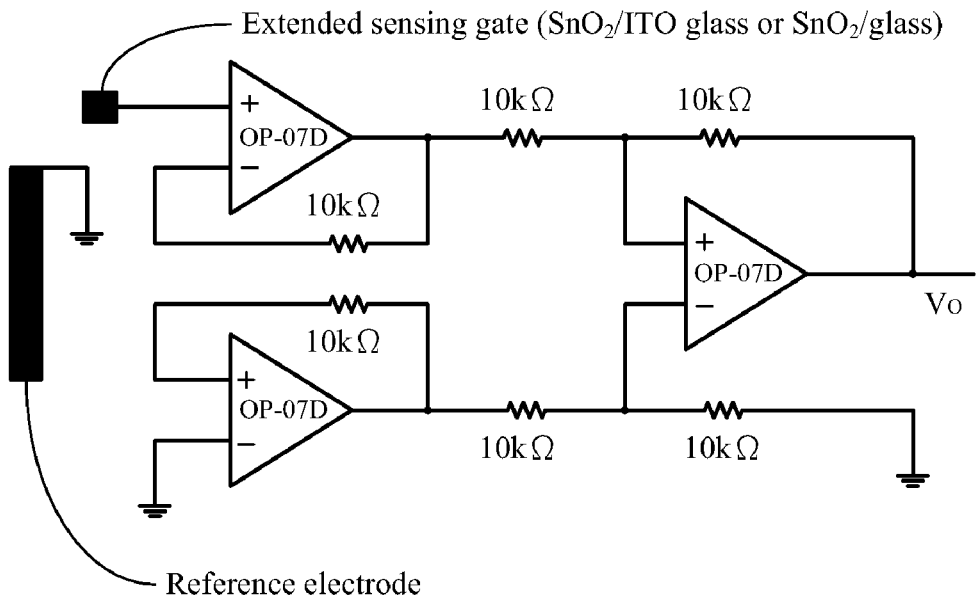
FIG. 3 schematically shows a measuring Apparatus of Ion Sensitive Electrode.
Figure 4:
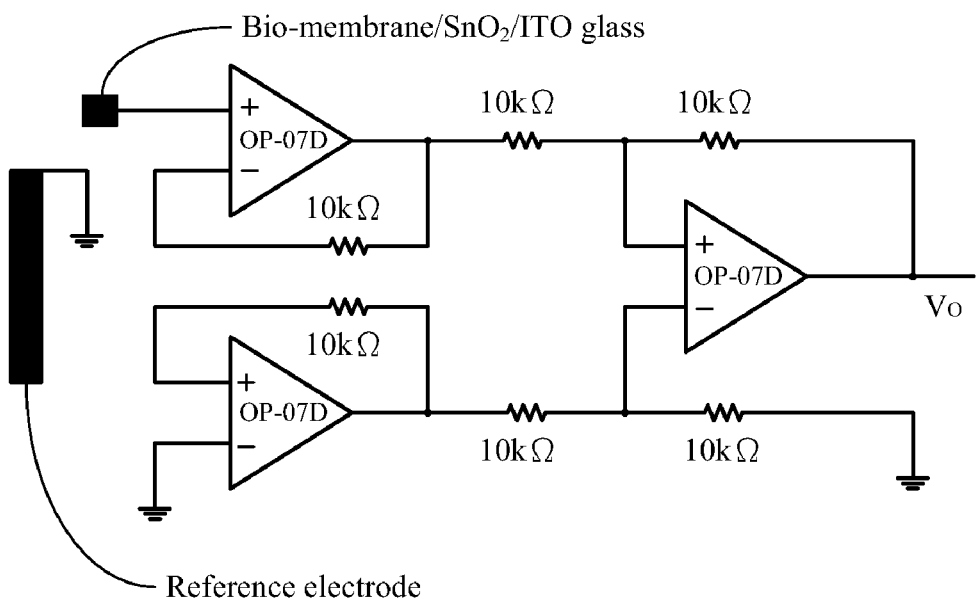
FIG. 4 schematically shows a measuring Apparatus of Biosensor.

FIG. 3 shows the utilization of the rear readout circuit to detect the voltage message for the analysis of acidity sensing message. FIG. 4 shows the utilization of the rear readout circuit to attain the sensor voltage message of the bio-sensing electrode.

Figure 5:
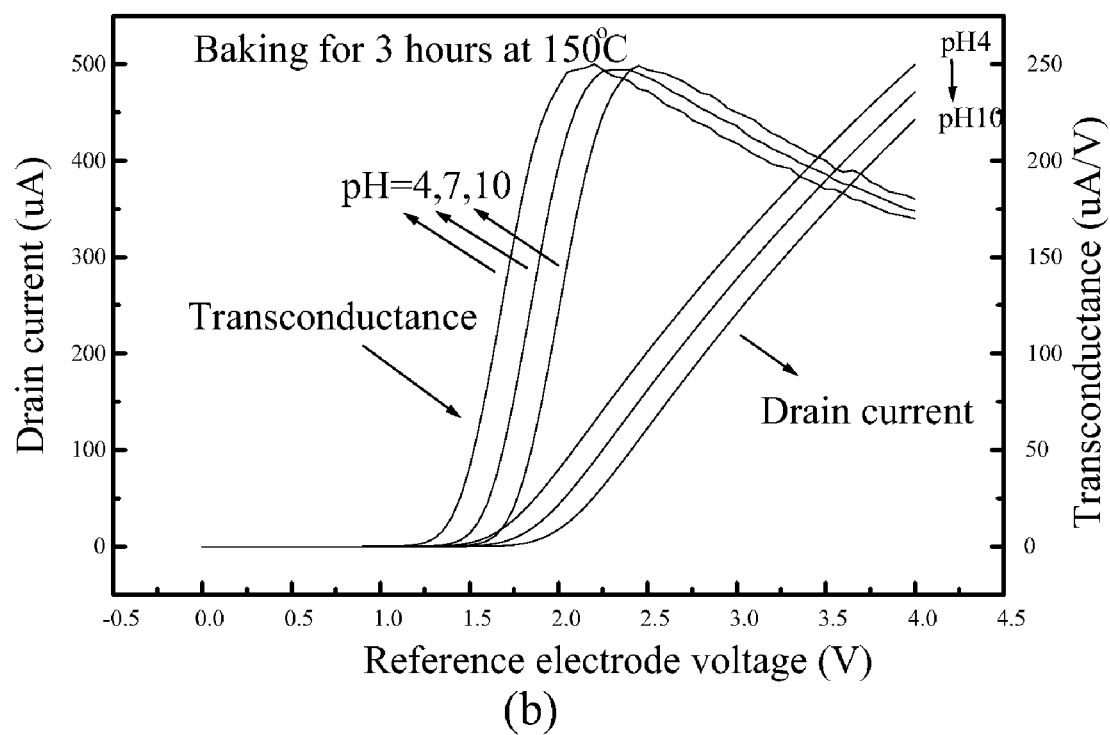
FIG. 5 schematically shows I-V Properties of pH Sensor with Micro Glass Base.
Figure 6:
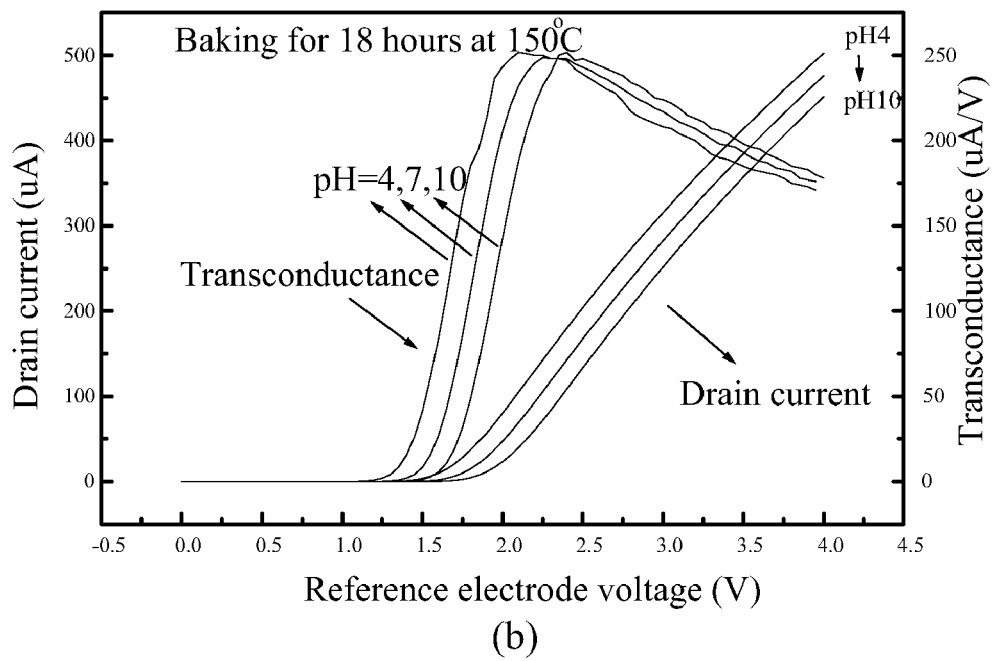
FIG. 6 schematically shows I-V Properties of pH Sensor with Corning Glass Base.

FIG. 5 shows the process of depositing sensitive thin film on to a micro glass slide, and placing the sensor element under 150° C. for 3 hours. This stabilizes the sensor and this sensor possesses acid sensitivity. FIG. 6 shows he process of depositing sensitive thin film on to a corning glass slide, and placing the sensor element under 150° C. for 18 hours. This stabilizes the sensor and this sensor possesses pH sensitivity. From FIGS. 5 and 6, it is discovered that sensor elements with the conductive metal—Aluminum, is capable of improving the stability after a 3-18 hour temperature treatment of 150° C.

Figure 7:
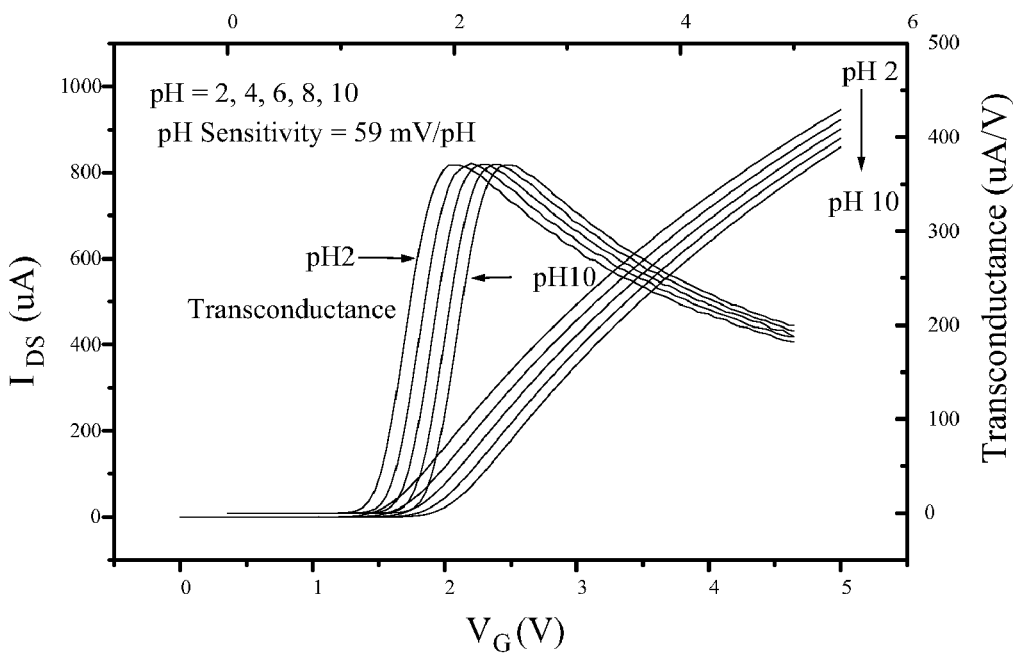
FIG. 7 schematically shows (SnO2/ITO glass) I-V Properties of pH Sensitive Electrode.
Figure 8:
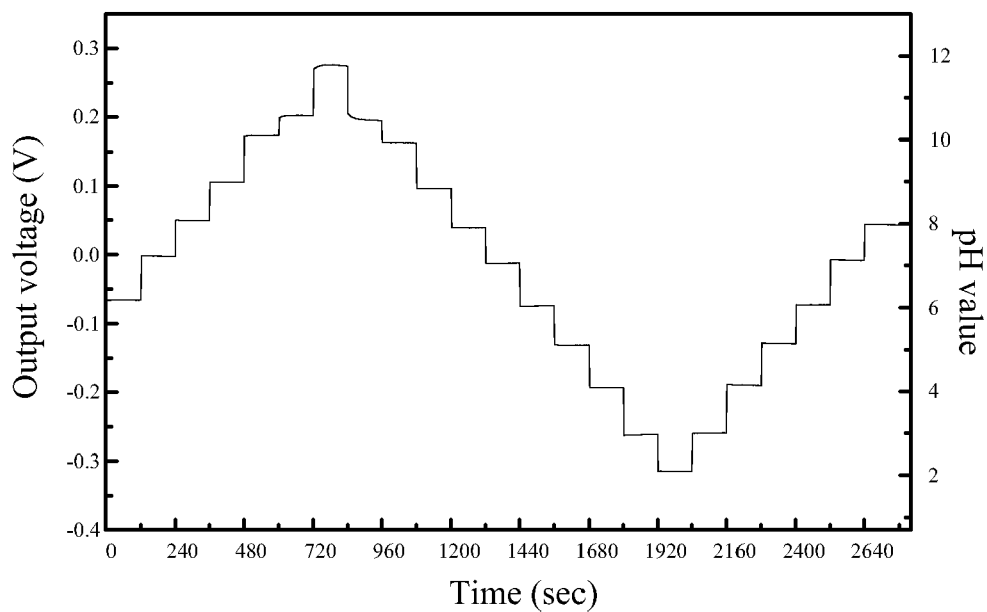
FIG. 8 schematically shows (SnO2/ITO glass) Properties of pH Sensitive Electrode.
Figure 9:
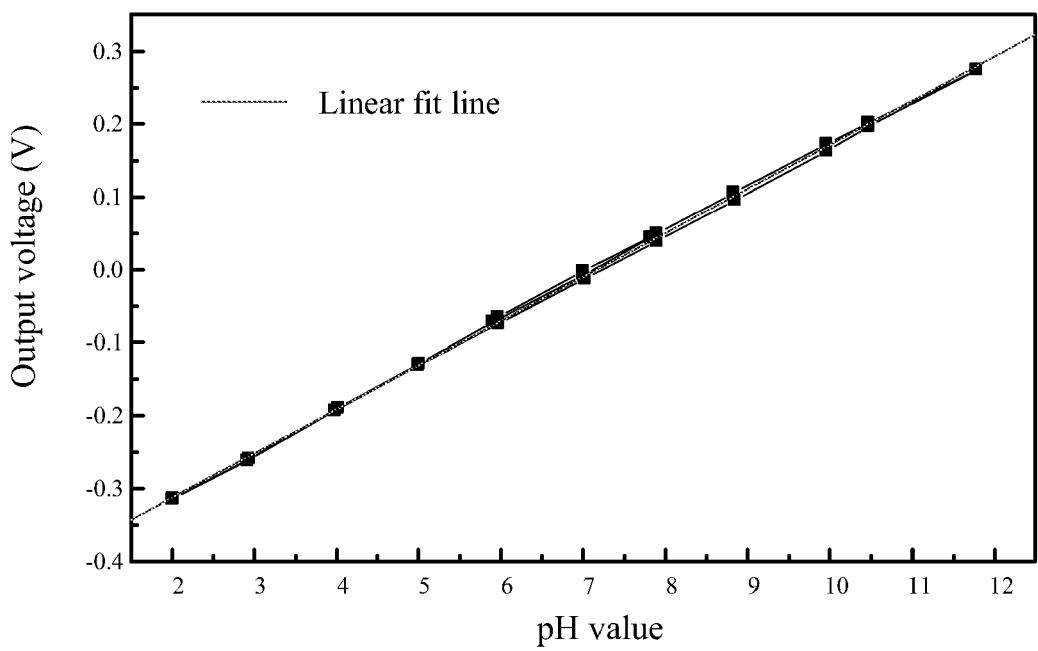
FIG. 9 schematically shows an (SnO2/ITO glass) Output Corrected Curve of Sensitive Electrode.

Shown in FIG. 7 is the deposition of tin oxide, solid thin film deposited on an ITO glass. Good pH sensitivity is already in place without temperature treatment. Shown in FIG. 8 is the transformation to voltage message using rear readout circuit. Tin oxide/ITO glass sensor generates different voltage message as the pH changes. FIG. 9 shows the linear output of the Tin oxide/ITO glass sensor. Combining FIGS. 7, 8 and 9, it is noted that between pH2 and pH 12, the Tin oxide/ITO glass sensor has a high sensitivity of 59.9 mV/pH, and the linear regression coefficient is over 0.999, an excellent linearity.

Figure 10:
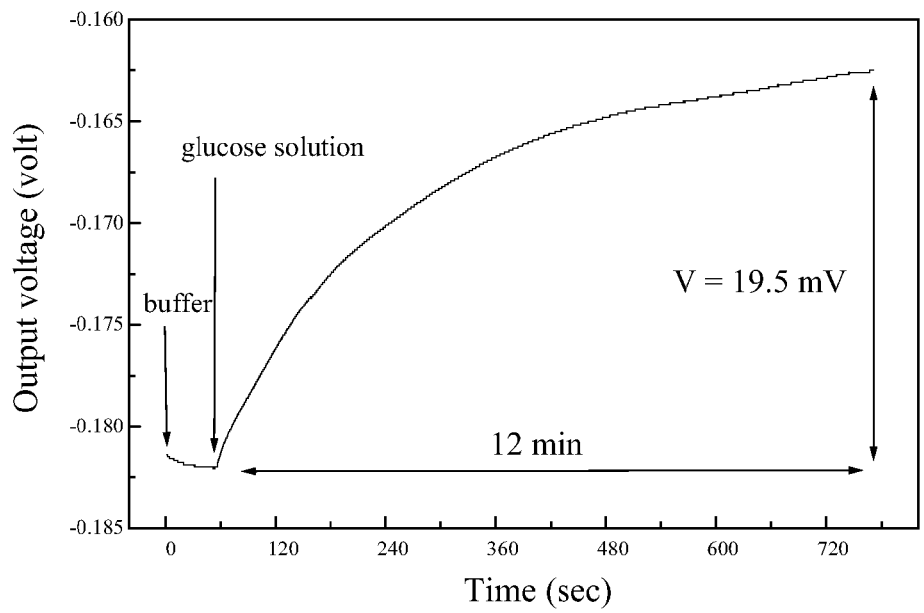
FIG. 10 schematically shows an Output Curve of Glucose Biosensor.
Figure 11:
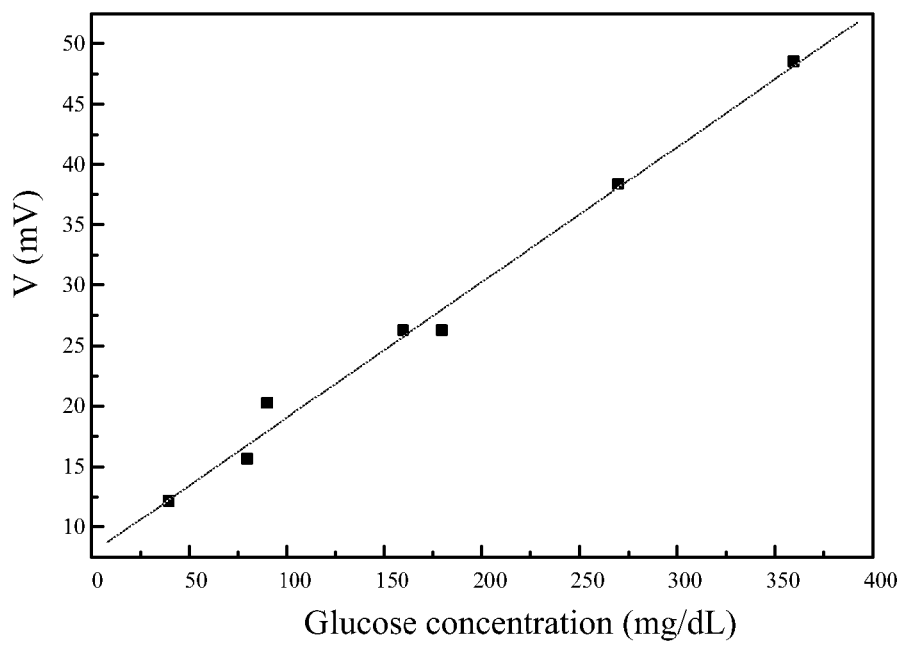
FIG. 11 schematically shows a Corrected Output Curve of Glucose Biosensor.

As shown in FIG. 10, the biosensor with an enzymatic thin film is placed into glucose solution. H+ is produced by the enzymatic reaction, and thus resulting in a voltage change. This method can be used to detect different glucose concentrations. As shown in FIG. 11, glucose solutions of different concentrations have a linear voltage output property. Therefore this bio-sensing element has can be used to detect glucose concentration and may be used to further research on biosensors.

Figure 12:
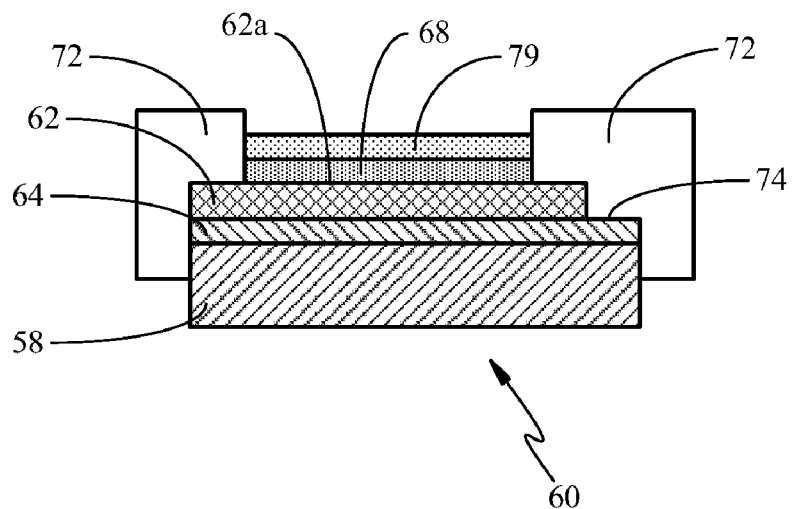
FIG. 12 shows a sectional view of a potentiometric glucose biosensor.

In another embodiment of the present invention, a potentiometric glucose biosensor is based on a SnO2/ITO glass pH sensor. A sensitive part of the SnO2/ITO glass pH sensor with enzyme membrane is shown in FIG. 12. The SnO2 layer 62 is deposited to have a thickness of 200 nm by using a sputtering method. Before the SnO2 layer 62 is deposited on an ITO glass layer 64, the ITO glass layer 64 is washed in the methyl alcohol solution and D.I. water for 20 min and 10 min, respectively.

Enzyme immobilization

Referring to FIG. 12, a coating process of a 3-glycidyloxypropyltri-methoxysilane (GPTS) layer 68 is illustrated as follows.

a. A potentiometric glucose biosensor 60 having a solid layer (e.g., a SnO2 layer 62) and an ITO glass layer 64 is cleaned with D.I. water for about 15 min.

b. 2 μl of the GPTS is dropped onto a sensing window 62a of the SnO2 layer 62.

c. The SnO2 layer 62, the ITO glass layer 64 and the dropped GPTS (also a GPTS layer 68) are cured at about 150° C. for about 2 hours.

d. After curing, the potentiometric glucose biosensor 60 having the GPTS layer 68 is washed by immersing it in a pH 7, 5 mM phosphate buffer solution for 10 min, to clean away the GPTS not bound to the sensing window 62a.

Figure 13:
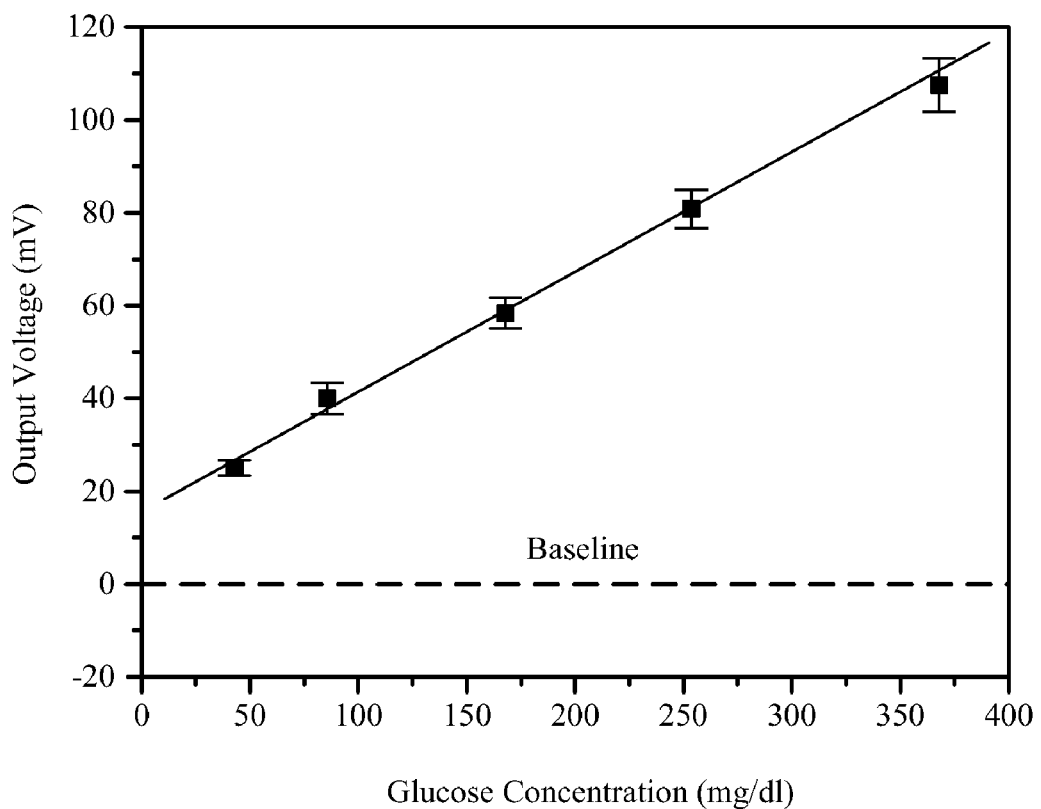
FIG. 13 shows a calibration curve of the potentiometric glucose biosensor.

FIG. 13 shows the calibration curve of the potentiometric glucose biosensor. The detecting step of each different glucose concentration is performed eight times. From the calculation, the reliability of the potentiometric glucose biosensor is obtained. By increasing the glucose concentration, the standard deviation increases.

As shown in FIG. 13, glucose solutions of different concentrations have a linear voltage output property. Therefore this biosensor may be used to detect different glucose concentrations and may be applied to other biosensor-related research.

The above disclosure provides many different embodiments, or examples, for implementing different features of the invention. Also, specific examples of components, and processes are described to help clarify the invention. These are, of course, merely examples and are not intended to limit the invention from that described in the claims.

While the invention has been particularly shown and described with reference to the preferred embodiment thereof, it will be understood by those skilled in the art that various changes in form and detail may be made therein without departing from the spirit and scope of the invention. For example, the selections of the 3-glycidyloxypropyltrimethoxysilane, the β-D-glucose oxidase and/or the polyvinyl alcohol bearing styrylpyridinium groups may be changed according to the detected object of the sensor.

What is claimed is:

1. A method of fabricating an electrode assembly of a sensor, the sensor having a field effect transistor, the electrode assembly being separated from the field effect transistor by only a conductive line, the sensor being functioned to detect different glucose concentrations, the method comprising: depositing a solid layer of tin oxide on a substrate board; placing .beta.-D-glucose oxidase and polyvinyl alcohol bearing styrylpyridinium groups in 100 .mu.l of sulfuric acid, to form an enzyme mixture; dropping the enzyme mixture on the solid layer of tin oxide; drying the enzyme mixture; exposing the enzyme mixture to a UV ray; drying and stabilizing the enzyme mixture; and immersing the enzyme mixture in a sulfuric buffer.

2. The method of claim 1, wherein the enzyme mixture is exposed to UV ray for about 20 minutes.

3. The method of claim 1, wherein the enzyme mixture is stabilized for about 4 hours.

4. The method of claim 1, wherein the enzyme mixture is immersed in a sulfuric buffer for about 1 hour.

\* \* \* \* \*